United States Patent
Cartier et al.

(10) Patent No.: US 10,526,464 B2
(45) Date of Patent: Jan. 7, 2020

(54) EXPANDED POLYMER POWDERS

(71) Applicant: Arkema Inc., King of Prussia, PA (US)

(72) Inventors: Laurent B. Cartier, Wayne, PA (US); Stephen Serpe, Media, PA (US)

(73) Assignee: Arkema Inc., King of Prussia, PA (US)

( * ) Notice: Subject to any disclaimer, the term of this patent is extended or adjusted under 35 U.S.C. 154(b) by 0 days.

(21) Appl. No.: 15/543,713

(22) PCT Filed: Jan. 12, 2016

(86) PCT No.: PCT/US2016/012974
§ 371 (c)(1),
(2) Date: Jul. 14, 2017

(87) PCT Pub. No.: WO2016/115086
PCT Pub. Date: Jul. 21, 2016

(65) Prior Publication Data
US 2018/0009961 A1    Jan. 11, 2018

Related U.S. Application Data

(60) Provisional application No. 62/103,229, filed on Jan. 14, 2015.

(51) Int. Cl.
*C08J 9/228*    (2006.01)
*A61K 8/88*    (2006.01)
*A61Q 19/00*    (2006.01)
*A61K 8/02*    (2006.01)

(52) U.S. Cl.
CPC .............. *C08J 9/228* (2013.01); *A61K 8/022* (2013.01); *A61K 8/0241* (2013.01); *A61K 8/0279* (2013.01); *A61K 8/88* (2013.01); *A61Q 19/00* (2013.01); A61K 2800/10 (2013.01); A61K 2800/412 (2013.01); A61K 2800/54 (2013.01); C08J 2205/052 (2013.01); C08J 2377/02 (2013.01)

(58) Field of Classification Search
None
See application file for complete search history.

(56) References Cited

U.S. PATENT DOCUMENTS

| | | | |
|---|---|---|---|
| 3,615,972 A | 10/1971 | Morehouse, Jr. et al. | |
| 4,022,719 A | 5/1977 | Okuyama et al. | |
| 4,028,287 A | 6/1977 | Sato et al. | |
| 4,397,799 A | 8/1983 | Edgren et al. | |
| 4,464,491 A | 8/1984 | Kosa | |
| 4,704,239 A | 11/1987 | Yoshimure et al. | |
| 4,828,542 A * | 5/1989 | Hermann | A41D 13/1146 15/104.93 |
| 5,206,012 A | 4/1993 | Farer et al. | |
| 5,925,380 A | 7/1999 | Roulier et al. | |
| 6,039,085 A | 3/2000 | Hsich | |
| 6,132,742 A | 10/2000 | Le Bras et al. | |
| 6,403,070 B1 * | 6/2002 | Pataut | A61K 8/0279 424/400 |
| 7,081,216 B2 | 7/2006 | Amin-Sanayei et al. | |
| 7,252,866 B2 | 8/2007 | Tang et al. | |
| 7,994,231 B2 | 8/2011 | Jacobs et al. | |
| 8,486,531 B2 | 7/2013 | Masuda et al. | |
| 2005/0276967 A1 * | 12/2005 | Prasad | B24B 37/24 428/314.8 |
| 2006/0083762 A1 * | 4/2006 | Brun | A61K 8/26 424/401 |
| 2009/0004457 A1 * | 1/2009 | Cho | B29C 44/12 428/305.5 |
| 2009/0048356 A1 | 2/2009 | Witten et al. | |

* cited by examiner

*Primary Examiner* — Ronak C Patel
(74) *Attorney, Agent, or Firm* — Thomas F. Roland

(57) ABSTRACT

The invention relates to small expanded polymer powder particles, and uses thereof. The expanded powder particles are formed by a non-melt process, resulting in individual expanded particles in the 5 to 100 micron range. The expanded powder particles are especially useful in cosmetic applications, as they provide a softer feel than a powder, and have a much higher surface area, making them highly absorbent for removing liquids and oils, as well as for use as excellent carriers and release agents for active ingredients.

5 Claims, No Drawings

EXPANDED POLYMER POWDERS

This application claims benefit, under U.S.C. § 119 or § 365 of PCT Application Number PCT/US2016/012974, filed Jan. 12, 2016, and U.S. Provisional Application No. 62/103,229, filed Jan. 14, 2015, these documents being incorporated herein by reference.

FIELD OF THE INVENTION

The invention relates to small expanded polymer powder particles, and uses thereof. The expanded powder particles are formed by a non-melt process, resulting in individual expanded particles in the 5 to 100 micron range. The expanded powder particles are especially useful in cosmetic applications, as they provide a softer feel than a powder, and have a much higher surface area, making them highly absorbent for removing liquids and oils, as well as for use as excellent carriers and release agents for active ingredients.

BACKGROUND OF THE INVENTION

Powders are commonly used in cosmetic formulations to provide specific textures and sensory feel, especially for cosmetics and skin care applications. The powders used may be inorganic minerals (such as mica, talc, kaolin, silica, etc.), may be organic-based materials (such as starch, cellulose, jojoba, etc.), or may be synthetic polymer powders (such as polyamides, polyurethanes, acrylics, polymeric silicones, polyolefins, etc.). Polyurethane and silicone powders are often present in high end cosmetics, due to their elastomeric and rubbery properties. The powders may be surface treated to enhance their physical properties, improve dispersion, increase/decrease hydrophobicity, and improve dispersion.

Due to bulk microporosity found in some of these powders (such as found in Orgasol® powders from Arkema Inc.), they can also be used as carriers of active ingredients, including but not limited to hyaluronic acid, lactic acid, ceramide, glycerin, etc. Arkema's ORGASOL® ultra-fine polyamide powders are microporous, and have open cells due to their manufacturing process. These powders have a very narrow particle size range that can be between 5 and 60 microns, depending on the grade.

Expanded polymers, also known as polymer foams, provide lighter, softer and more flexible structures, with increased surface area, and lower density. Polymer foams are used to provide thermal and acoustical insulation, as well as strong, lighter, lower density structures. Polymeric foams are generally formed, as described in U.S. Pat. No. 8,277,913, by melting the polymer, adding a chemical or physical blowing agent (directly or in a master batch), the blowing agent expands the volume of the melted polymer forming small voids, and when cooled, the gas bubbles are either trapped (in a closed cell foam), or dissipate to create inter-connected voids (in an open cell foam). Polyamide foams are described, for example in U.S. Pat. Nos. 4,464,491, 4,028,287, 4,022,719 and 6,039,085

Unfortunately, the foams formed from a melt cannot be shredded, cut or ground in a manner to produce consistent foam particles in the 5 to 100 micron region. Even cryogenic grinding of foams does not result in small individual foam particles of the 5 to 100 micron range.

Polymer foams have been formed by methods other than from the melt. In U.S. Pat. No. 7,081,216, an open cell polymer foam was formed from a polymer latex or polymer aqueous suspension by first freezing the aqueous polymer dispersion or suspension, followed by thawing. This freeze-thaw polymer foam resulted in a large foam molded object, and not in individual, small polymer foam particles. US 2009/0048356 describes a process for introducing a gas into a polymer, in which polymer granules are exposed to an inert gas, under pressure and at a temperature between the glass transition (Tg) point and the melting point for a semi-crystalline or crystalline polymer, or a temperature below the Tg for an amorphous polymer. The gas impregnated polymer is then melt-processed, where the impregnated gas expands into a foamed, shaped article. A similar process is described in U.S. Pat. No. 7,994,231, in which a polyamide resin is subjected to high pressure under an inert gas, the temperature is raised to soften the polymer, the pressure is then lowered and temperature is lowered below the softening point, The partially expanded polyamide resin is again heated above its softening point under pressure, then the pressure reduced while the polymer remains above the softening point. This results in a closed cell polyamide film. The Examples are all done on polymer slabs.

It has now been found that polymeric powders can be expanded without undergoing a melt process, to produce very small, individual expanded powder particles in the 5 to 100 micron range. These expanded powders are lighter, softer and have more surface area (are more absorbent) than the solid polymer particles. The expanded polymer powders also exhibit elastomeric properties with improved compaction and cushioning, higher oil absorption, and higher active ingredient loading.

SUMMARY OF THE INVENTION

The invention relates to expanded thermoplastic particles comprising a thermoplastic matrix having closed voids, where the expanded particles have a volume average particle size of from 1 to 100 microns.

The invention further relates to a process for forming the expanded polymer particles, comprising the steps of
a) heating polymer particles having an average diameter of from 1 to 95 microns are above their softening point,
b) exposing said heated particles to an inert gas above atmospheric pressure to force the inert gas into the polymer particle,
c) reducing the pressure—allowing the gas to expand, then
d) cooling the polymer particles below the softening point—to produce a closed-cell foam.

The invention also relates the use of the expanded particles, in applications such as cosmetic compositions and food-contact compositions.

DETAILED DESCRIPTION OF THE INVENTION

The invention relates to the formation and use of small powder expanded particles having a volume average size in the 5 to 100 micron range. The expanded particles contain closed cells, or closed voids in their structure.

All references cited herein are incorporated by reference. Unless otherwise stated, all molecular weights are weight average molecular weights as determined by Gas Permeation Chromatography (GPC), and all percentages are percentage by weight.

The term "copolymer" as used herein indicates a polymer composed of two or more different monomer units, including two comonomers, terpolymers, and polymers having 3 or more different monomers. The copolymers may be random or block, may be heterogeneous or homogeneous, and may be synthesized by a batch, semi-batch or continuous process.

By expanded polymer, foam, or polymer foam, as used herein, is meant an expanded polymer containing closed-cell voids, having a density that is at least 5% less than the density of the solid, un-expanded polymer.

Powder Composition

The expanded polymers of the invention can be formed from any thermoplastic polymer that is in the form of a powder having a volume average particle size of less than 100 microns, with a preferred range of 1 to 50 microns, more preferably 1-30 microns, more preferably 5-20 microns, and most preferably 5-15 microns. Once the particle is expanded it will be in the 1-100 micron volume average range, and for cosmetic use the final expanded particles should have a volume average particle size of less than 30 microns, and preferably in the 5-20 micron range. Particle size can be determines using ISO 13319 with a Coulter counter. Micron-sized powder can be made by a suspension or emulsion polymerization, followed by drying (spray dry, drum dry) to obtain individual, free-flowing micron sized particles.

The powder particles can be spherical, ovoid, irregular, or any other shape. In one embodiment, the polymer particles may be porous, having open-cell void networks (such as ORGASOL® fine powders from Arkema Inc. Such open-cell porous particles could be further expanded by the present invention to create powder particles having both open and closed-cell voids.

In another embodiment, the powder particles are in the form of fibers, and especially in microfibers. Useful fibers for the invention are those with diameters in the range of 1 to 100 microns, preferably 1 to 50 microns and most preferably from 3 to 20 microns The fiber length can be any length, up to several meters long, preferably less than 1 meter in length. In one embodiment, fibers of from 0.1 to 5 mm are used. The expanded fibers can produce an increase in fiber volume, without any increase in fiber weight. This could be useful, for example, in mascara applications and eyelash extension. The expanded, light-weight fibers, such as polyamides, fluoropolymers, PEEK and PEKK, could find use in industrial applications, where good chemical and wear resistance are desired.

In one embodiment, the thermoplastic can be in the form of microfibers, having a fiber diameter of less than 100 microns, preferably less than 50 microns, and more preferably less than 30 microns.

The polymer particles useful for the invention are thermoplastic polymers, and are semi-crystalline to amorphous. Thermoset and crystalline polymers are unable to flow at temperatures near the melting point, with no change in the structure below the melting point. Semi-crystalline polymers are useful in the invention. Amorphous and low-crystalline polymer are preferred, due to their increased ability to flow and change shape at temperatures between the glass transition temperature and the crystalline melting point, and below the glass transition temperature for an amorphous polymer.

Useful polymer for the invention include, but are not limited to: amorphous and semi-crystalline polyamides (including but not limited to polyamide 6, PA 11, PA 12, copolyamide 6.6, 6.12, 6.10, 10.10, and 10.12), polyether-block amides, polyester-block amides, amorphous and semi-crystalline semi-crystalline polyolefins (such as polyethylene and polypropylene), semi-crystalline and amorphous polyvinylidene fluoride, amorphous acrylics (such as polymethyl methacrylate (PMMA) and copolymers thereof), poly-lactic acid (PLA), PMMA/PLA alloys, polyesters, polyether ether ketone (PEEK), polyether ketone ketone (PEKK), and thermoplastic polyurethane. Preferred polymers for use in the invention include PA11, PA6.12, PA12, and PMMA. A blend, alloy or mixture of two or more different thermoplastic materials in particulate form is also anticipated by the invention.

Process

The process for expanding the thermoplastic polymer is described in US 2009/0048356. The process includes heating the polymer particles above their softening point, exposing them to an inert gas above atmospheric pressure to force the inert gas into the polymer particle, reducing the pressure—allowing the gas to expand, then cooling the polymer particles below the softening point—to produce a closed-cell foam.

The thermoplastic polymer powder is exposed to an inert gas at a pressure above atmospheric pressure and above its softening point, in a pressure vessel. The pressure applied may be any pressure sufficient to dissolve gas into the polymer particles. The heating and pressure increase can be done simultaneously, or in any order. The polymer particles can be exposed to the heat and high pressure for any amount of time that is sufficient to achieve the desired level of gas absorption into the polymer particles. The absorption of the gas can be increased by raising the temperature as high as is practical. Increased temperature reduces the amount of time needed to saturate the polymer particles, and also increases the amount of gas that can be absorbed. Full saturation of the polymer particles is not required for the particles to be expanded, and the level of expansion can be controlled by varying the level of saturation of the particles. Inert gases useful for the invention include, but are not limited to nitrogen, carbon dioxide, argon, nitrogen. The polymer can be heated above its softening point by the use of heat, radio frequency, and irradiation. By "softening point" as used herein is meant the temperature where semi-crystalline particles are preferably at a temperature above the Tg, but below the melting point, while amorphous polymer particles are heated to below the Tg of the polymer. The softening temperature must be low enough so the particles do not stick or fuse to each other, but high enough that significant levels of gas are absorbed.

The key phase-change temperature of these polymers (Tg or Tm) is shifted to higher temperatures at increased pressures, so it is possible to carry out the gas absorption process at temperatures above the Tg or Tm at ambient temperatures. On the other hand, the absorbed gasses act as plasticizers of the polymer, and may cause the polymer particles to fuse together at lower temperatures.

The gas in the closed cell voids will dissipate over time, the dissipation can be slowed by refrigeration. Once the gas is released, the voids in the cooled polymer particle remain, creating an expanded, closed-cell polymer particle, which can be considered a foamed particle.

Properties

The expanded polymer particles of the invention have closed cells. In the case where porous (open-cell) particles are used as a starting material, the final expanded polymer particles will have both open cells and closed cells.

The closed-cell expanded polymer particles, are also known as particular foams, with particle sizes of less than 100 microns. The expanded particles of the invention have a reduction in density of at least 5 percent, based on the un-expanded polymer particles, preferably at least a 10 percent density reduction, and more preferably a density reduction of at least 20 percent. In a preferred embodiment, the expanded polymer particles have a density of at least 30% below that of the non-expanded polymer particles, and the expansion can result in a density decrease (particle volume increase), of from 30 to 95%, preferably from 50 to 90% and more preferably 60 to 80%. The density reduction is due to the increase in particle size of from 10 to 500 percent (a five times increase in the diameter of the particle results in a 125 times increase in the volume and a corresponding decrease in the density of the expanded particle).

These expanded particles are light weight, and have a soft feel. The expanded particles are also more elastic than the starting particles, meaning they can be deformed and return to their original shape. If the starting article size is in a very narrow range, such as for ORGASOL® fine powders, the final expanded powders will also be in a narrow particle size distribution.

Formulations and Uses

One advantage of the expanded polymer particles is that they contain no chemical blowing agent. For uses where chemical blowing agents or solvents would be detrimental, such as in cosmetics or food-contact applications, the expanded polymer particles of the invention These expanded powders are lighter, softer and have more surface area (are more absorbent) than the solid polymer particles. The expanded polymer powders are useful in cosmetic applications, as they exhibit improved compaction, cushioning, higher oil absorption, and higher active ingredient loading, making them useful in cosmetic applications—providing a softer feel, absorbing more fluids, and delivering more active ingredients, than a solid polymer powder. Useful cosmetic applications for the expanded polymer powder include, but are not limited to, skin care formulations; sun care creams and lotions; color cosmetics such as lipstick, mascara, and foundations); hair care (shampoo, conditioners, hair dyes and tints, and hair treatments).

These same properties of the expanded polymer powders of the invention, make them useful in other industrial applications. One of ordinary skill in the art, based on the present description, can imagine many useful applications of the expanded polymer powders. For example, industrial applications include, but are not limited to, additives for inks, additives for coatings, transfer paper, as a light-weight filler in other polymers, and micro-sponge absorbents,

EXAMPLES

1. A 10 micron PA11 (polyamide 11) powder from Arkema (ORGASOL Green Touch) is placed in a pressure vessel into which nitrogen is introduced to a pressure of 670 bar. The temperature is raised to 170° C. and the pressure was maintained for 3 hours. The pressure was then reduced to 15 bar of nitrogen at a temperature of 150° C. to allow gas expansion. The pressure vessel is cooled and the residual pressure was released to atmospheric to give an expanded powder of PA11.

2. A 12 micron PA12 powder from Arkema (ORGASOL 2002 EXD NAT COS type S) is placed in a pressure vessel into which nitrogen is introduced to a pressure of 670 bar. The temperature was raised to 160° C. and the pressure was maintained until the powder was saturated with nitrogen. The pressure was then reduced to 15 bar of nitrogen at a temperature of 140° C. The pressure vessel was cooled and the residual pressure was released to atmospheric to give an expanded powder of PA12.

Within this specification embodiments have been described in a way which enables a clear and concise specification to be written, but it is intended and will be appreciated that embodiments may be variously combined or separated without parting from the invention. For example, it will be appreciated that all preferred features described herein are applicable to all aspects of the invention described herein.

Aspects of the invention include:

1. Expanded thermoplastic particles comprising a thermoplastic matrix having closed voids, wherein said expanded particles have a volume average particle size of from 1 to 100 microns, preferably from 1-50 microns, more preferably from 1-30 microns, and most preferably from 5-20 microns.

2. The expanded particles of claim 1, wherein the thermoplastic matrix is selected from the group consisting of amorphous and semi-crystalline polyamide 6, PA 11, PA 12, copolyamide 6.6, 6.12, 6.10, 10.10, and 10.12), polyether-block amides, polyester-block amides, amorphous and semi-crystalline semi-crystalline polyolefins (such as polyethylene and polypropylene), semi-crystalline and amorphous polyvinylidene fluoride, amorphous acrylics (such as polymethyl methacrylate (PMMA) and copolymers thereof), polylactic acid (PLA), PMMA/PLA alloys, polyesters, polyether ether ketone (PEEK), polyether ketone ketone (PEKK), and thermoplastic polyurethane, polylactic acid (PLA), PMMA/PLA alloys, polyesters, thermoplastic polyurethane, and copolymer and mixtures thereof.

3. The expanded particles of either of claims 1 and 2, wherein said expanded particles have a density that is from 5 to 95%, preferably from 20 to 90%, more preferably from 30 to 90%, and most preferably from 50 to 90% less than that of the un-expanded particles.

4. A process for forming the expanded polymer particles of claims 1-3, comprising the steps of
a) heating polymer particles having an average diameter of from 1 to 95 microns are above their softening point,
b) exposing said heated particles to an inert gas above atmospheric pressure to force the inert gas into the polymer particle,
c) reducing the pressure—allowing the gas to expand, then
d) cooling the polymer particles below the softening point—to produce a closed-cell foam.

5. A composition comprising the expanded particles of claims 1-3.

6. The composition of claim 5, wherein said composition is a cosmetic composition.

7. The composition of claims 5 and 6, wherein said composition is a composition in contact with food.

What is claimed is:

1. Expanded thermoplastic individual particulate foam particles wherein each individual particle comprises a thermoplastic matrix having closed voids, wherein said expanded, individual particular foam particles have a volume average particle size of from 1 to 100 microns, said thermoplastic matrix being selected from the group consisting of amorphous and semi-crystalline polyamide 6, PA 11, PA 12, copolyamide 6.6, 6.12, 6.10, 10.10, and 10.12), polyether-block amides, polyester-block amides, amorphous and semi-crystalline polyolefins, semi-crystalline and amorphous polyvinylidene fluoride, polylactic acid (PLA), polyesters, polyether ether ketone (PEEK), polyether ketone ketone (PEKK), thermoplastic polyurethane, and mixtures thereof, wherein said expanded particles have a density that is from 5 to 95% less than that of the un-expanded particles, wherein said expanded particles have an average particle size from 5-20 microns and the individual particulate foam particles further comprise open cells.

2. The expanded particles of claim 1, wherein said expanded particles have a density that is from 20 to 90% less than that of the un-expanded particles.

3. The expanded particles of claim 1, wherein said expanded particles have a density that is from 30 to 90% less than that of the un-expanded particles.

4. The expanded particles of claim 1, wherein said expanded particles have a density that is from 50 to 90% less than that of the un-expanded particles.

5. The expanded particles of claim 1, wherein said individual particulate foam particles are individual, free-flowing micron sized particles.

* * * * *